United States Patent [19]
Smith

[11] Patent Number: 5,170,783
[45] Date of Patent: Dec. 15, 1992

[54] CRYOTHERAPEUTIC PROCEDURE

[76] Inventor: Kirby Smith, 3640 Blakeford Way, NE., Marietta, Ga. 30062

[21] Appl. No.: 822,379

[22] Filed: Jan. 17, 1992

Related U.S. Application Data

[60] Division of Ser. No. 545,295, Jun. 28, 1990, which is a continuation of Ser. No. 408,761, Sep. 18, 1989, abandoned, which is a continuation of Ser. No. 294,428, Jan. 9, 1989, abandoned, which is a division of Ser. No. 172,578, Mar. 24, 1988, abandoned.

[51] Int. Cl.$^5$ .............................................. A61F 7/00
[52] U.S. Cl. .................................. 128/400; 128/382
[58] Field of Search .............. 128/384, 400, 402, 403, 128/DIG. 12, DIG. 3, DIG. 27, DIG. 20, 898, 379, 82.1, 656, 382; 604/4; 606/192

[56] References Cited

U.S. PATENT DOCUMENTS

| | | | |
|---|---|---|---|
| 267,435 | 11/1882 | Leiter | 128/400 |
| 1,732,380 | 10/1929 | Sarason | 128/403 |
| 2,026,747 | 1/1936 | Nemzek | 128/400 |
| 2,832,336 | 4/1958 | Davis et al. | 128/402 |
| 2,930,594 | 3/1960 | MacCrackon | 128/400 |
| 3,628,537 | 12/1971 | Berndt | 128/402 |
| 3,683,902 | 8/1972 | Artemenko | 128/400 |
| 3,871,381 | 3/1975 | Roslonski | 128/400 |
| 4,335,726 | 6/1982 | Kolstedt | 128/400 |
| 4,474,538 | 10/1984 | Schmid-Schërbeln et al. | 128/DIG. 3 |
| 4,739,767 | 4/1988 | Lahr | 128/656 |

FOREIGN PATENT DOCUMENTS 3304697 12/1983 Fed. Rep. of Germany ...... 128/402

*Primary Examiner*—William H. Grieb
*Assistant Examiner*—Mark S. Graham
*Attorney, Agent, or Firm*—Caesar, Rivise, Bernstein, Cohen & Pokotilow, Ltd.

[57] ABSTRACT

A cryotherapeutic procedure is disclosed for treating an injury with a cold compress system that has a flexible application bag coupled with a cold liquid supply container via a flexible tube. The flexible application bag is secured about a body member with the bag in contact with the area of injury. The supply container is elevated above the bag so that cold liquid gravitates from the supply container into the application bag causing it to fill and to apply cold and pressure to the area of injury. The height of the supply container above the application bag is adjusted to establish the desired pressure exerted by the application bag upon injury.

6 Claims, 2 Drawing Sheets

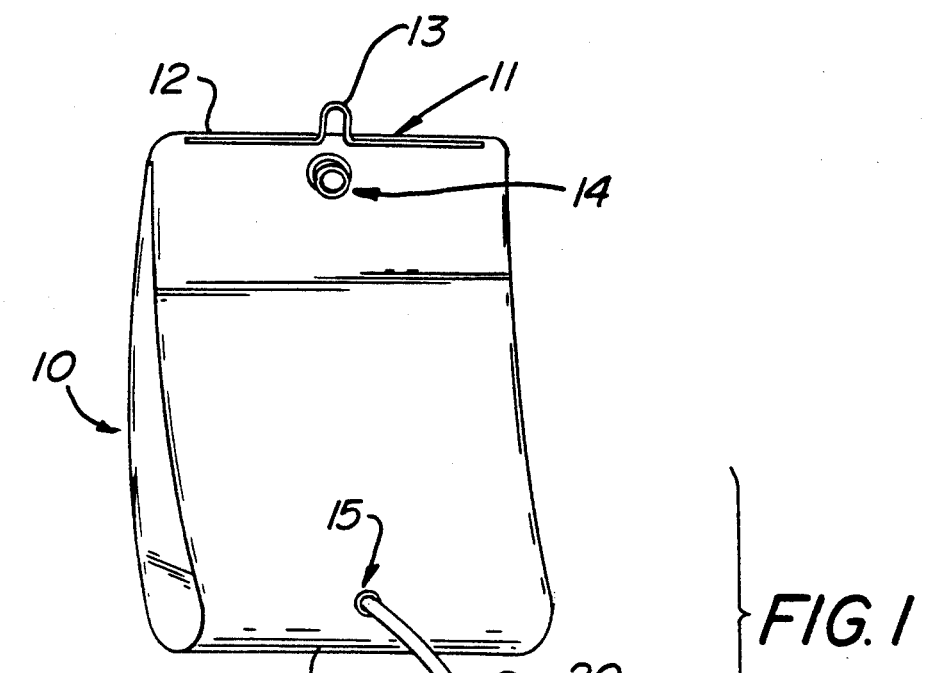
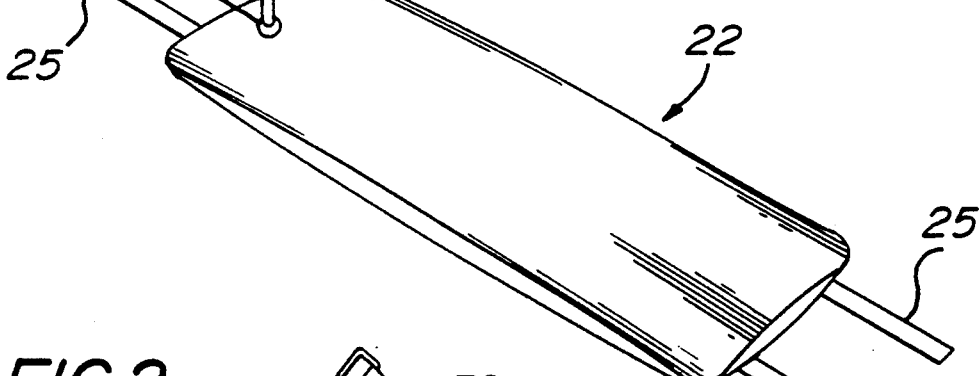
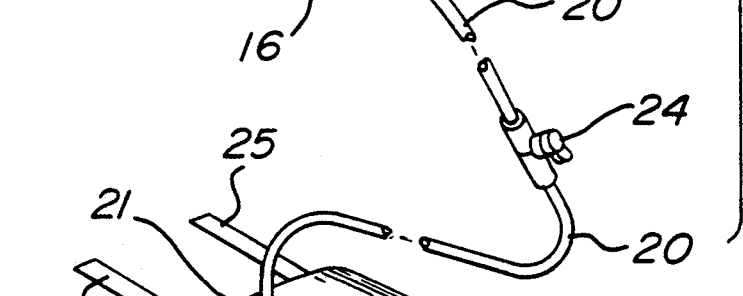
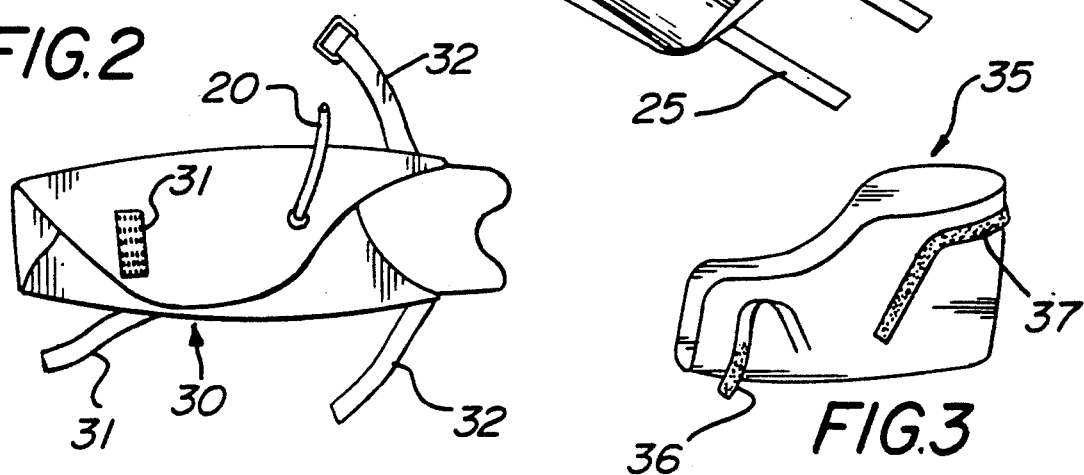

CRYOTHERAPEUTIC PROCEDURE

PRIOR U.S. APPLICATIONS CLAIMED

This application is a divisional application of 07/545,295, filed Jun. 28, 1990; which in turn is a continuation of 07/408,761, filed Sep. 18, 1989, now abandoned, which in turn is a continuation of 07/294,428, filed Jan. 9, 1989, now abandoned, which in turn is a division of 07/172,578, filed Mar. 24, 1988, now abandoned.

TECHNICAL FIELD

This invention relates to devices and procedures for use in applying cold and compression to body injuries such as trauma induced and postoperative edema.

BACKGROUND OF THE INVENTION

The use of cold therapy, now termed cryotherapy, is ancient. Indeed, Hippocrates is reported to have noted in 400 B.C. that the application of cold injuries tends to decrease swelling and to reduce pain by producing numbness. The topical application of pressure to injuries is also well known as a cryotherapeutic technique. Particularly in sports medicine, today cryotherapeutic procedures are commonly used to reduce edema and tissue damage.

Cryotherapy is also practiced as a postoperative procedure in hospitals with the use of electrically powered apparatuses that create compression and which circulate cold fluids. Outside of institutions such as hospitals, however, the use of electrically powered machines is often impractical or not feasible machines is often impractical or not feasible at all as where no source of electric power is available. Also, where long term treatment is needed for ambulatory patients the coupling of such equipment to the patients as they move about is cumbersome. For the foregoing reasons cold compresses of simple construction have ben devised for applying cryotherapy in home and outdoor environments.

Ice packs and bandages have provided the simplest forms of cold compresses. More sophisticated compresses have included reusable cold packs designed to be wrapped around body members such as that known as The Ice Down sold by I.C.E. Down Corporation of Delmar, California. Exemplary of the more advanced compression only type products is that known as the Air-Stirrup ankle brace which permits normal flexion to reduce swelling. Other devices have utilized small bottles of pressurized refrigerants for introduction into specially designed boots or the like to provide both a chemical cold pack as well as some degree of compression. A cold compress sold under the name Compac has also been recently marketed as an alternate to ice bags. It is designed to be stored in a refrigerator for later use by being molded about an injury.

Though small cold compresses are seen now to have been developed that provide improvements over simple ice bags and the like, they have not been capable of providing substantial pressure. Compression devices have essentially remained in the domain of the larger type apparatuses that are connected to electrically powered air compressors. Thus, were a relatively small cold compress system to be devised by which both cold and compression could be applied in a substantial and yet easy manner, a distinct advance in the art would be achieved. It is to the provision of such therefore that the present invention is primarily directed.

SUMMARY OF THE INVENTION

In one form of the invention a cold compress system comprises a flexible application pack adapted to be wrapped about an injured body member and which bears fastening means for holding the application bag in place. A cold water supply container is provided from which a flexible tube extends to the application pack to provide fluid communication therebetween. The system also includes valve means for controlling the flow of water between the application pack and supply container.

In another form of the invention, a cold compress system comprises a reservoir into which a cold liquid may be introduced, an inflatable bag, and fastening means for holding the inflatable bag in a position wrapped securely about an injured body member as the bag is inflated. The system also has means for transferring cold liquid between the reservoir and the bag while the bag remains wrapped securely about the body member. Means are also provided for controlling the transfer of cold liquid between the reservoir and the bag.

A cryotherapeutic procedure is provided for treating an injury. In accordance with the procedure an inflatable bag is wrapped about the injury and secured in place so that bag inflation and deflation, caused by infusion and expulsion of a liquid into and out of the bag, alters the pressure applied by the bag to the injury. A cold liquid is then introduced into the bag from a reservoir elevated above the bag until the bag is substantially fully inflated in its secured configuration.

In yet another form of the invention a cryotherapeutic procedure is provided for treating an injury with a cold compress system of the type that has a flexible application bag coupled with a cold liquid supply container via a flexible tube. The procedure comprises the steps of securing the flexible application bag about a body member with the bag in contact with the injury and elevating the supply container above the bag whereby cold liquid gravitates from the supply container into the application bag. This action causes the bag to fill and to apply cold and pressure to the area of injury. The height of the supply container is adjusted above the application bag to establish the desired pressure exerted by the application bag upon the injury.

BRIEF DESCRIPTION OF THE DRAWING

FIG. 1 is a perspective view of a cold compress system embodying principles of the in which may be utilized in practicing a cryotherapeutic procedure of the invention.

FIG. 2 is a top view of an application pack in an alternative form configured into the shape of a boot.

FIG. 3 is a perspective view of an application pack or bag of another boot-shaped configuration.

DETAILED DESCRIPTION

Figure 4:
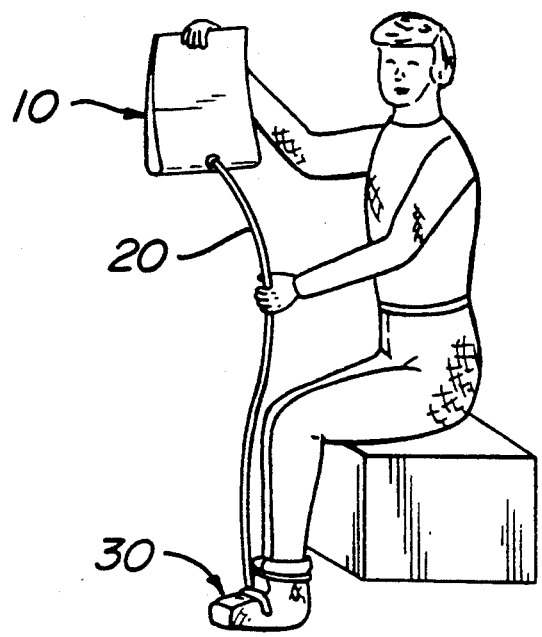
FIG. 4 illustrates a person performing the inventive procedure with the cold compress system while seated.

With reference next to the drawing, there is shown in FIG. 1 a cold compress system which comprises a flexible supply container or reservoir 10 that has a top end 11 that is heat sealed about a wire 12. The wire is formed with a hook 13 for use in hanging the reservoir from an ancillary support. The container 10 is also provided with a port 14 located above its open upper end 11, and which is here shown temporarily closed by a plug, and an outlet 15 located adjacent its bottom end 16.

An elongated, flexible tube 20 extends from the outlet 15 to an inlet 21 of a flexible application pack or bag 22 of generally rectangular configuration A hand operable flow control valve 24 is provided in the tube 20 for use in controlling the flow of liquid between the reservoir and the application pack. The pack 22 has straps 25 that bear releasibly interlockable masses of fibers such as Velcro.

In preparation for use, the valve 24 is turned to its off position and ice water, with or without a supply of ice cubes, is poured into the reservoir 10 through the port 14. The flexible application pack 22 is then wrapped about an area of injury such as a body limb like a leg or an arm. With the application bag in its deflated configuration wrapped snuggly about the limb, it is secured in place with the Velcro bearing straps 25 placed one upon the other in mating engagement.

Next the reservoir 10 is elevated above the now secured application bag and the valve 24 opened whereupon cold water flows down the reservoir and into the application bag. As this occurs the application bag expands and inflates until it is constrained from further significant inflation by the straps 25. As the bag inflates in its constrained state, it commences to apply pressure and cold to the injured body limb. Once the bag has reached its expansion limits imposed by the fastening of the straps 25 this pressure is adjusted by adjusting the height or elevation of the reservoir, with some cold water reminding in it, above the application bag.

Figure 5:
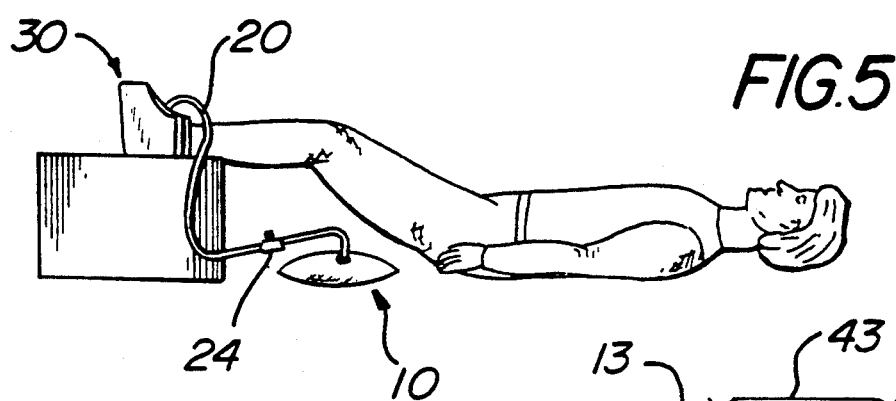
FIG. 5 illustrates a person performing the inventive procedure with the cold compress system while lying down.
Figure 6:
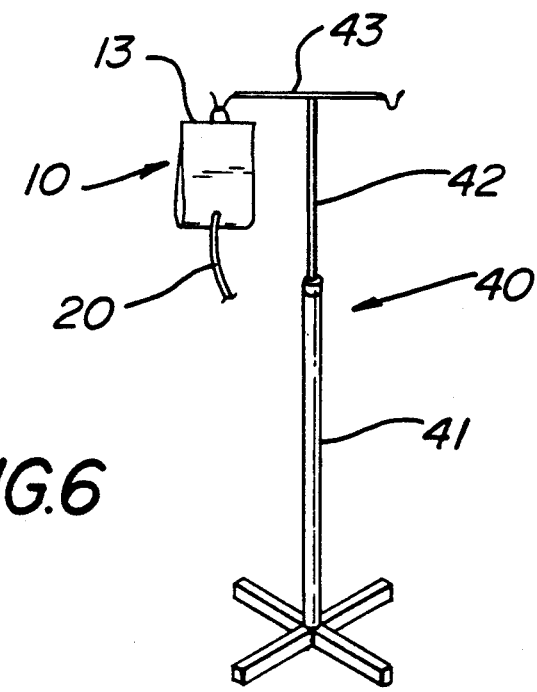
FIG. 6 is a perspective view of an I.V. stand supporting a reservoir component of the cold compress system.

A person using the cold compress system just described way, for example, sit while holding the reservoir bag 10 above himself as illustrated in FIG. 4. With valve 24 open the pressure exerted by the boot-shaped application bag or pack here, which is shown in more detail in FIG. 2, is established by the height at which the person holds the reservoir 10. In other words, if the pressure is too great he simply lowers the bag. Conversely, to increase the pressure he elevates the bag. He may continue to hold the bag at a desired elevation and pressure or he may close valve 24 so that the elevation of the reservoir then ceases to effect the pressure applied by the application bag. This enables him, for example, to lie down with his foot propped up as shown in FIG. 5 and with the reservoir laid on the ground or floor. Alternatively, the reservoir 10 may be suspended as from a stand 40 as shown in FIG. 6. In this case, the stand is a conventional I.V. stand that has a height adjustable member 42 that projects out of a tube base 41. The bag 10 is suspended from a hanger rod 43 mounted atop the member 42.

To terminate the therapy the straps 25 may be simply pulled apart and the application bag unwrapped from about the injury. This may be done without any operation of the valve or movement of the reservoir bag. Of course, the pressure may be more gradually decreased by lowering the reservoir bag with the valve 24 opened thereby causing the pressure applied by the bag to decrease. Even a reverse flow of cold water may occur from the application bag back to the reservoir. In any event it is seen that the system is essentially a closed system although the top of the reservoir bag may be opened to receive ice cubes and cold water, or other cold liquid.

In FIG. 2 an application pack 30 is shown in a configuration that differs from the configuration of the pack 22 illustrated in FIG. 1. The application pack here is shaped to be wrapped about a foot and then secured in place by overlapping two mating strips of Velcro 31 and by buckling straps 32 about an ankle. Thus, the application bag is formable into the configuration of a boot with end portions overlapping one another and held together by the Velcro strips and the ankle strap. The boot-shaped application pack 30 where is the only difference in the cold compress system illustrated in FIG. 1 and is placeable in the same manner in fluid communications with a reservoir by means of the flexible tube 20.

In FIG. 3, an application pack 35 is shown of another configuration but still in the general shape of a boot. In this embodiment only an insubstantial amount of overlay may occur in wrapping the pack about a foot since the application bag is semi-rigidly shaped into an open-top boot. Velcro bearing straps 36 are provided for the toe end while Velcro bearing straps 37 are provided for adapting around the ankle portion of the person in securing the heel portion of the pack.

Cold compress systems of the type just described are capable of applying compressive forces of between 0–130 mm of Hg. Filled with ice water the bag typically applies a temperature of approximately 36°–38° F. to an area of injury. Compression has been found to be achievable as follows:

| HEIGHT OF TOP BAG | mm Hg Pressure | | |
| --- | --- | --- | --- |
| ABOVE BOTTOM BAG | FOOT | ANKLE | KNEE |
| 1 Foot | 22 | 24 | 26 |
| 2 Feet | 45 | 46 | 48 |
| 3 Feet | 68 | 66 | 66 |
| 4 Feet | 90 | 87 | 88 |
| 5 Feet | 114 | 110 | 110 |
| 6 Feet | 134 | 131 | 130 |

It thus is seen that a cold compress system and cryotherapeutic procedure is now provided that overcomes limitations of those of the prior art. It should be understood, however, that many modifications, additions, and deletions may be made to the specific embodiments illustrated without departure from the spirit and scope of the invention as set forth in the following claims.

I claim:

1. A method of therapeutically treating an injured body part, said method including the steps of:

locating a flexible, inelastic application pack on the injured body part to be treated;

employing fastening means associated with the application pack for securing the application pack in conformity with the injured body part; thereafter introducing a pressurizing cold liquid to said application pack from pressurizing liquid supply means via a conduit coupled between the application pack and the pressurizing liquid supply means; said pressurizing liquid supply means comprising a container for holding the cold liquid therein, said cold liquid being provided to said application pack by the steps of:

(a) supporting the container above the application pack so that said cold liquid is transported by gravity to said application pack via said conduit; and (b) controlling the flow of the cold liquid through the conduit means to said application pack; controlling a desired amount of pressure applied to the injured body member through the application pack by establishing a predetermined elevation of the container above the application pack, and thereafter operating valve means to maintain said desired amount of pressure irrespective of the elevation of said container.

2. The method of claim 1 wherein the step of locating the application pack on the injured body part is achieved by wrapping the pack about said body part in the region overlying the injury.

3. The method of claim 1 wherein the fastening means includes cooperating locking surfaces, one of said surfaces being formed on a flexible strap constituting part of the application pack, said step of securing the application pack to said body member being achieved by manipulating the strap into a position in which the cooperating locking means engage each other.

4. The method of claim 1 wherein the application pack is in the general shape of a boot having portions adapted to overly the foot and ankle regions of a person, including the step of locating the application pack on the foot of a person and thereafter employing the fastening means for securing the application pack into conformity with the foot and ankle region of the person, prior to providing the pressurizing cold liquid to said application pack.

5. The method of claim 1 wherein the container constituting the pressurizing liquid supply means includes a removable top, including the additional steps of removing the top of the container; introducing water and ice into said container and thereafter closing said top.

6. The method of claim 1 wherein said valve means is in the form of a valve communicating with the conduit in a region between the pressurizing liquid supply means and the application pack, including the additional step, after a desired pressure has been established by adjusting the elevation of the container relative to the application pack, of closing said valve.

* * * * *